United States Patent [19]
Janke

[11] Patent Number: 5,044,360
[45] Date of Patent: Sep. 3, 1991

[54] ORTHOSIS WITH VARIABLE MOTION CONTROLS

[75] Inventor: Wayne R. Janke, Pasadena, Calif.

[73] Assignee: United States Manufacturing Company, Pasadena, Calif.

[21] Appl. No.: 485,962

[22] Filed: Feb. 27, 1990

Related U.S. Application Data

[63] Continuation-in-part of Ser. No. 457,018, Dec. 26, 1989, abandoned.

[51] Int. Cl.$^5$ ............................................. A61F 5/00
[52] U.S. Cl. ............................ 128/80 H; 128/80 C; 128/77; 403/113; 403/117; 623/47; 623/39
[58] Field of Search ............... 128/80 R, 80 H, 80 C, 128/88, 77; 623/27, 39, 40, 47; 403/113, 117; 16/341

[56] References Cited

U.S. PATENT DOCUMENTS

| | | | |
|---|---|---|---|
| 3,187,347 | 6/1965 | Terron | 128/88 |
| 3,779,654 | 12/1973 | Horne | 128/80 C |
| 4,353,361 | 10/1982 | Foster | 128/80 C |
| 4,655,201 | 4/1987 | Pirmantgen | 623/39 |

Primary Examiner—Richard J. Apley
Assistant Examiner—Lynne A. Reichard
Attorney, Agent, or Firm—Christie, Parker & Hale

[57] ABSTRACT

A releasable controlled-motion ankle-foot orthosis includes an elongated shell adapted for releasable attachment to the lower leg above the ankle joint, a foot support adapted for releasable attachment to the foot, and lateral and medial controlled-motion ankle joint assemblies attached to the shell and to the foot support in alignment with the axis of rotation through the ankle joint. Each ankle joint assembly includes a rigid support plate affixed at one end to the shell, extending across the ankle joint, and affixed at the other end to the foot support. Sets of cam members in matching pairs are used interchangeably for controlling range of motion in plantar flexion and dorsiflexion. Each individualy selectable cam member is rotatably mounted to the support plate for contact with a stop on the support plate to control angular motion. Each cam member has a unique combination of anterior and posterior cam surfaces that contact or rotate into contact with corresponding anterior and posterior portions of the stop to provide different selective angles of rotation in plantar flexion and dorsiflexion, including extended range of motion in plantar flexion and dorsiflexion, a stop in dorsiflexion combined with controlled angular motion in plantar flexion, and vice versa, no motion in either plantar flexion or dorsiflexion, and a (+)(−) cam to accommodate alterations to lessen angular motion control.

17 Claims, 4 Drawing Sheets

Fig. 1

Fig. 2

ORTHOSIS WITH VARIABLE MOTION CONTROLS

CROSS REFERENCE

This is a continuation-in-part of application Ser. No. 07/457,018, filed Dec. 26, 1989, which is incorporated herein by this reference, now abandoned.

FIELD OF THE INVENTION

This invention relates generally to orthotic devices, and more particularly, to a selectable controlled-motion orthosis. A preferred embodiment is an ankle-foot orthosis having controlled angular motion for facilitating the rehabilitation process required for ankle sprains and other injuries to the ankle joint or for post-surgical needs.

BACKGROUND OF THE INVENTION

In the past, a variety of orthotic devices have been developed for supporting an injury to a bodily joint during the rehabilitation process. The present invention will be described in relation to an orthotic device for supporting the ankle joint, although the invention is applicable to orthotic devices for supporting other bodily joints.

There are various types of orthoses that permit limited ambulation of a patient during treatment of injuries such as fractures or ankle sprains or other injuries to the ankle joint. Severe ankle injuries such as an ankle fracture are normally treated by holding the foot and ankle immobilized in a rigid cast during the initial period of rehabilitation. A cast is uncomfortable because it is heavy and is not removable during its long period of use. It also limits the mobility of the patient.

After the cast is removed, a special light weight brace can be worn to increase patient mobility, while providing the necessary support to prevent twisting or other undue stress on the injured joint. These light weight orthotic devices can permit limited rotational motion of the ankle while the brace is worn. This provides a substantial benefit to the patient during the healing process when compared with a fixed cast. One orthotic device of this type is the tibia/ankle orthosis disclosed in U.S. Pat. No. 4,587,962.

Another type of brace used during the rehabilitation process is an ankle fracture walker disclosed in U.S. Pat. No. 4,771,768. The walker allows a controlled angular range of ankle motion in dorsiflexion and plantar flexion during weight-bearing on the ankle joint, while the ankle joint is supported by the walker, and while the patient walks at a normal walking gait controlled by the walker. As a result, the ankle fracture walker greatly enlarges the methods of treatment of ankle fractures during the rehabilitation process. Ankle fracture walkers normally include a rigid shell that fits around and under the foot, with a curved sole on the bottom of the shell to permit a rocking heel-to-toe motion of the foot during use. In the controlled motion walker, the rocker attaches to the leg of the patient by rigid or semi-rigid uprights extending along the lateral and medial sides of the leg above the ankle joint. The uprights attach to doubleaction ankle joints having rigid support bars that extend upwardly from both sides of a rigid plate on the base of the rocker. The plate is fastened to the rocker by screws. The double-action joint can be adjusted throughout the rehabilitation process to allow maximum mobility of the ankle joint during weight-bearing, depending upon the type of injury involved and the patient's progress during healing. Rehabilitation is functionally better for the patient and total rehabilitation time is reduced when compared with patients using prior art fixed-angle walkers.

A further type of orthotic device disclosed in U.S. Pat. No. 4,517,968 is used for treating ankle sprains. This device can be used for many sports injuries, such as ankle sprains that are not placed in a cast. This device immobilizes the injured joint by use of flexible lateral and medial support members extending along opposite sides of the injured joint. A foot support pivots about a fixed axis for hinging the lateral and medial support members to the foot base. With the user's foot in the foot supporting base, and the support members extending along the lateral and medial sides of the leg, a bandage can be wrapped tightly around the support members above the ankle joint. This immobilizes the ankle joint against lateral and medial movement, while providing limited resistance against torsion, and while also allowing forward and backward rotation about the ankle joint.

The '768, '962 and '968 patents described above are each owned by United States Manufacturing Company, the assignee of this application.

The present invention recognizes a need for a light weight ankle-foot orthosis that can effectively immobilize the ankle joint against lateral and medial movement, while providing a level of resistance against torsion, and also while allowing an adjustable range of motion in dorsiflexion and plantar flexion. There is also a need for uniformly distributing the pressure around the ankle joint, ensuring uniform fit and comfort of the orthosis, and providing a means for effectively making range of motion changes in a reliable light weight orthosis.

SUMMARY OF THE INVENTION

Briefly, one embodiment of this invention provides a controlled motion ankle-foot orthosis comprising an elongated shell adapted for releasable attachment to the lower leg above the ankle joint, a foot support adapted for releasable attachment to the foot, and lateral and medial controlled motion ankle-joint assemblies attached to the shell and to the foot support in alignment with an axis of rotation through the ankle joint. Each ankle joint assembly includes a rigid support plate affixed at one end to the shell, extending across the ankle joint, and affixed to the other end of the foot support. A set of cam members in matching pairs (for the lateral and medial sides of the orthosis) is used interchangeably for controlling range of motion in plantar flexion and dorsiflexion. Each individually selectable cam member is rotatably mounted to the support plate for contact with a stop on the support plate to control angular motion in plantar flexion and dorsiflexion. Each cam member has a unique combination of anterior and posterior cam surfaces that contact or rotate into contact with corresponding anterior and posterior portions of the stop to provide selective means of controlling different angles of rotation in plantar flexion and dorsiflexion. This set of cam members includes extended range of motion in plantar flexion and dorsiflexion; a stop in dorsiflexion combined with controlled angular motion in plantar flexion, and vice versa; and no motion in either plantar flexion or dorsiflexion.

Thus, by selection of the proper pair of cams, the orthosis, once fabricated, can be adjusted with varying degrees of motion during the useful life of the orthosis.

The invention is particularly useful as a versatile means for controlling the patient's treatment with a light weight orthosis throughout the rehabilitation process. The orthosis is easily adjustable, the cams are effective in providing reliable controlled stops in both directions of rotation, and the orthosis can be manufactured at a reasonable cost. These and other aspects of the invention will be more fully understood by referring to the following detailed description and the accompanying drawings.

DETAILED DESCRIPTION

Figure 1:
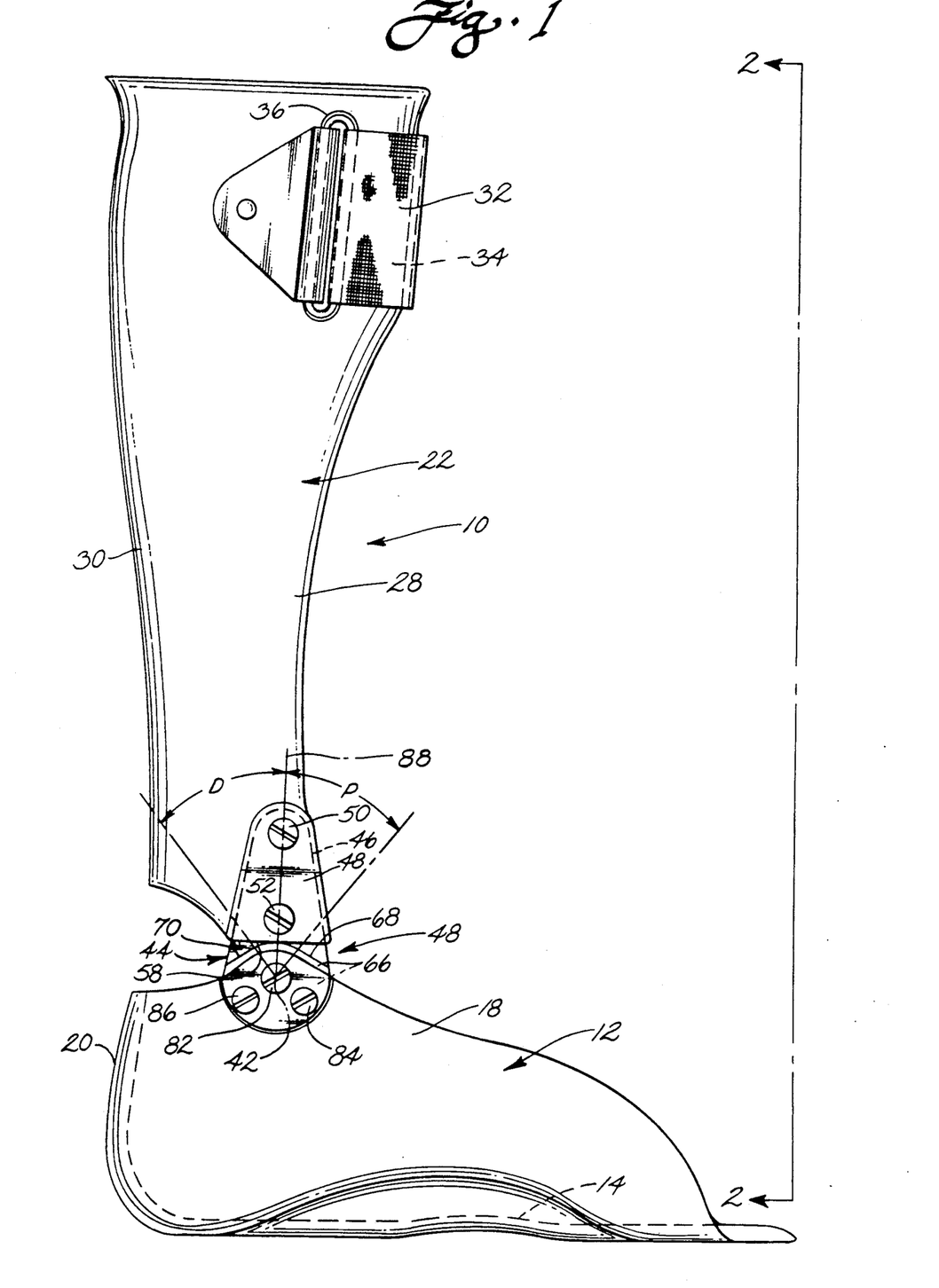
FIG. 1 is a side elevation view illustrating an anklefoot orthosis according to principles of this invention.
Figure 2:
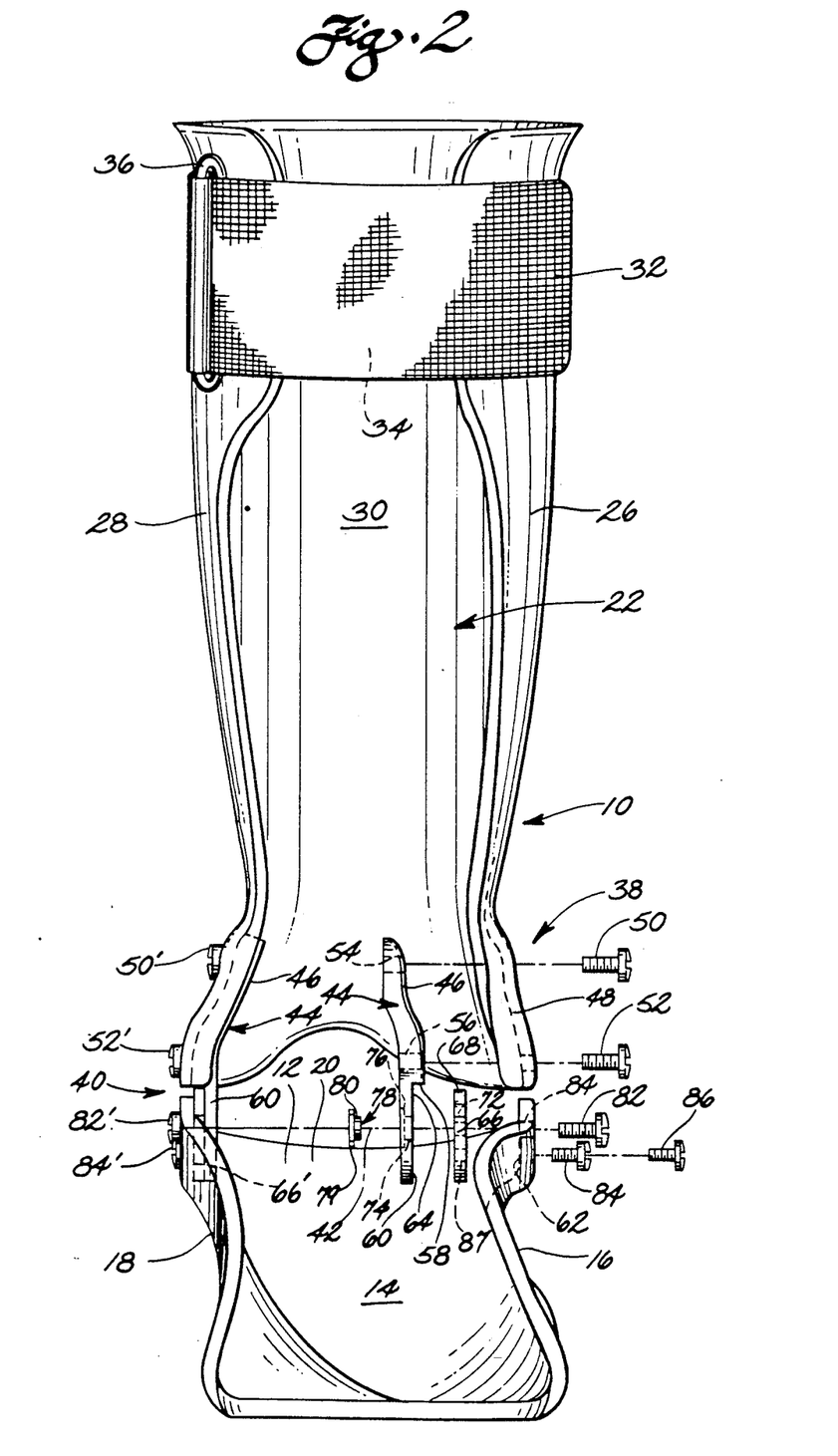
FIG. 2 is an anterior, partly exploded elevation view, taken on line 2—2 of FIG. 1.

FIGS. 1 and 2 illustrate components of an anklefoot orthosis 10 according to principles of this invention. The orthosis includes a brace or shell 12 for supporting the user's foot. The foot supporting shell includes a foot plate 14 for supporting the bottom of the foot, vertical lateral and medial side walls 16 and 18 for extending around lateral and medial sides of the foot, respectively, and a rounded posterior wall 20 for fitting around the heel. The foot-supporting shell is preferably made from a hard, relatively stiff plastic material such as polypropylene. The foot-supporting shell conforms closely to the shape of the foot and provides a light weight means of rigid support for the bottom, sides and rear of the user's foot.

An elongated upright lower leg-supporting shell 22 extends vertically upwardly above the lateral and medial side walls of the foot support. The lower leg support comprises a continuous wall of U-shaped configuration having lateral and medial sides 26 and 28 for extending along opposite sides of the lower leg above the ankle joint, and a rounded rear wall section 30 extending around the calf region of the user's leg. The front of the lower leg shell is open for ease of applying the device to the user's lower leg. A flexible strap 32 with suitable Velcro fasteners 34 is passed through a loop 36 affixed to one side of the lower leg shell for use in securing the shell around the lower leg. The lower leg-supporting shell is made from vacuum formed material such as polyproplyene.

The lateral and medial sides of the lower leg shell 22 are hinged to lateral and medial sides of the foot support 12 through lateral and medial controlled motion ankle joint assemblies 38 and 40 according to principles of this invention. Each selectively adjustable ankle joint assembly is identical (with the exception of the curve), making them interchangeable. Therefore, the description to follow with respect to the medial ankle joint assembly will suffice for the lateral ankle joint assembly as well.

The ankle joint assembly is best understood by referring to FIGS. 3 through 7 in addition to FIGS. 1 and 2. The ankle joint assemblies provide corresponding hinged pivot points aligned on a common axis through the axis rotation of the ankle joint. The hinge axis of rotation through the ankle joint is shown at 42.

Figure 3:
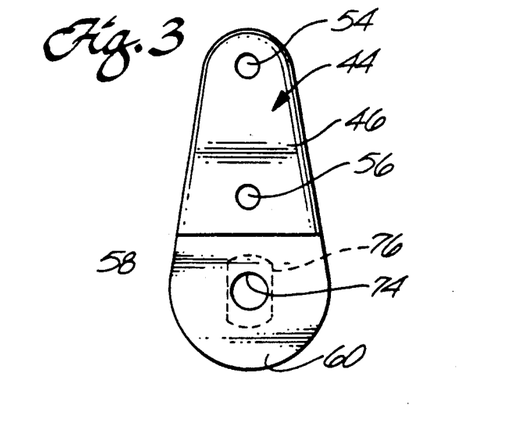
FIG. 3 is a medial/lateral elevation view of a rigid support plate portion of a controlled motion joint assembly.

Each hinge joint assembly includes an elongated rigid support plate 44 having an upper portion 46 adjacent the inside face of a molded upper socket portion 48 on the lower medial wall portion of the lower leg support immediately above the ankle joint. The support plate is made from a light weight metal such as aluminum. The upper portion of the rigid support plate fits into the socket 48. A pair of threaded fasteners 50 and 52 extend through corresponding vertically spaced apart holes in the socket portion of the leg support. The fasteners are threaded into corresponding internally threaded holes 54 and 56 in the support plate for tightening the upper portion 46 of the support plate 44 to the inside of the socket portion 48 of the lower leg support. Thus, the walls of the socket portion 48 of the lower leg support extend continuously around and encase the outer face of the upper portion 46 of the rigid support plate 44. Because of its rigid attachment, the rigid support plate 44 rotates with rotational motion of the lower leg support 22.

The rigid support plate 44 further includes an elongated shoulder 58 projecting from an outer face of the support plate and extending across the width of the support plate. In use, this shoulder faces downwardly toward the ankle joint and extends both anteriorly and to posteriorly of the axis 42 through the ankle joint.

A lower portion 60 of the rigid support plate 44 extends downwardly and is spaced from the inside face of a molded lower socket portion 62 of the foot supporting shell 12. A face of the lower portion 60 of the support plate 44 is recessed at 64 to form a narrow space between the recessed face 64 and the inside face 62 of the shell. This space is occupied by interchangeable cam members 66, described below.

As shown best in FIG. 2, the support plate 44 is contoured from top to bottom with a curvature that matches the curvature of the ankle joint so that the support plate's attachment to the orthosis does not create undue pressure on the ankle joint during use. The support plate 44 when viewed anteriorly/posteriorly illustrates one variation of the configuration of these devices with respect to lateral (medial applications of the ankle support). Other configurations are also possible, including a curved support plate on the medial side and a straight support plate on the lateral side.

A narrow cam member 66 is removably mounted in the recessed space at 64 and the inside face 62 of the foot support. The cam member is made from a light weight metal such as aluminum. The cam member 66 is secured to the inside face 62 which is a molded projecting recessed area of the foot support overlying the ankle joint. The lower portion 60 of the support plate combined with the cam member occupy this recessed ankle region of the foot-supporting shell. A notch 77 in the base of the cam is engaged with the molded projections in the recessed ankle portion of the foot support to resist rotation of the cam relative to the foot support.

Figure 4:
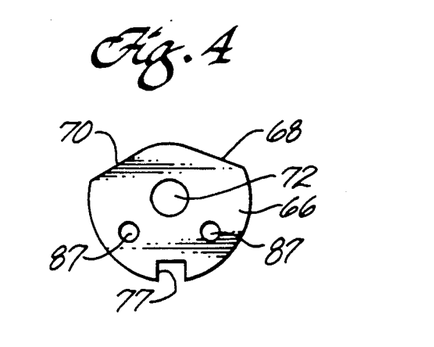
FIG. 4 is an elevation view of a cam member of the assembly.
Figure 5:
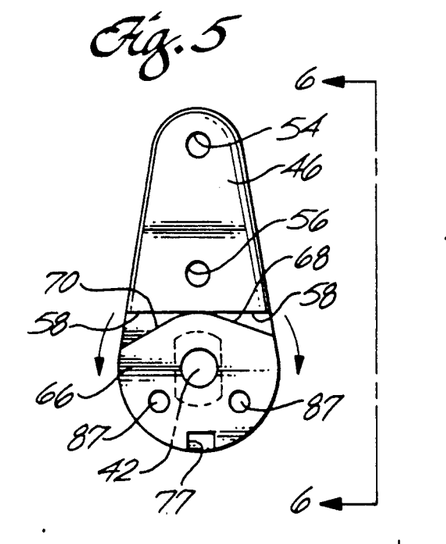
FIG. 5 is an elevation view illustrating the cam member assembled to the rigid support plate.
Figure 6:
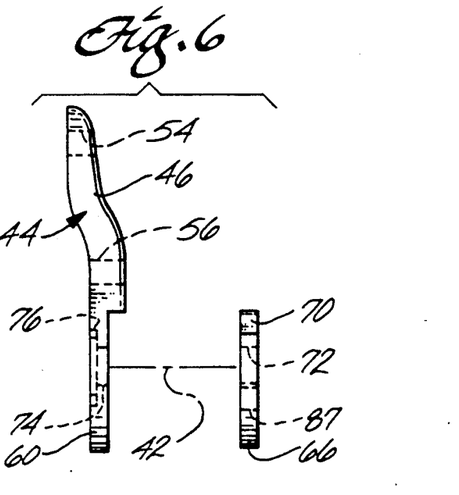
FIG. 6 is an exploded anterior/posterior elevation view taken on line 6—6 of FIG. 5.
Figure 7:
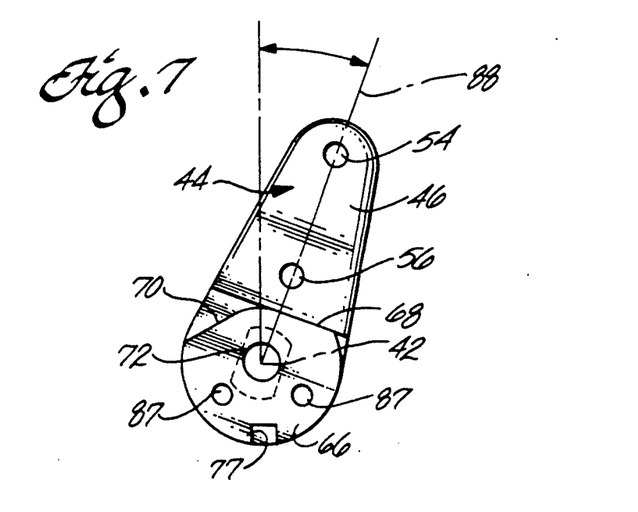
FIG. 7 is a medial/lateral elevation view similar to FIG. 5 but illustrating rotation of the support plate relative to the cam member.

The cam member 66 has a pair of angled anterior and posterior cam surfaces 68 and 70 extending along an upper edge of the cam member. These cams have flat peripheral edge surfaces as shown in FIG. 4. In one embodiment, these cam surfaces extend on angles with respect to a horizontal plane defined by the shoulder 58 of the support plate. The cam 66 shown in FIG. 1 is one example of several other configurations of the cam members described in more detail below with respect to the illustrations in FIGS. 8 through 17. A large central opening 72 extends through the cam member and is aligned on the axis 42 through the ankle joint. This opening is also aligned with an opening 74 extending through the lower portion of the rigid support plate 44. The opening 74 is then stepped up to form an opening 76 with flat sides in the rear face of the support plate. A T-nut 78 extends into the composite openings 76 and 74 of the support plate. The T-nut includes a rectangular flange 79 that fits into the flat-sided opening 76 to resist rotation of the nut relative to the support plate. The T-nut further includes a rounded sleeve 80 which is internally threaded and extends through the opening 74 in the support plate and the opening 72 in the cam member 66 when fastened. A threaded fastener 82 fastens the foot shell 12 to the lower leg support shell 22 via articulation between the cam member 66 secured in place between the inside wall 62 of the foot support and the lower portion 60 of the support plate 44. The fastener 82 extends through an opening 84 in the side wall 62 of the foot support and is then threaded into the internally threaded sleeve 80 of the T-nut 78 which is seated in the bore 76 extending through the lower opening 74 of the portion 60 of the support plate and the opening 72 of the cam 66. The fastener is tightened to rigidly but releasably affix the foot shell to the lower leg support shell. This means of attachment confines the cam member to rotation about the axis 42 through the ankle joint. The cam member is able to rotate about this axis relative to the fixed lower portion of the support plate 44. The cam member 66 is secured to the inside wall of the foot support by threaded fasteners 84 and 86 extending through corresponding openings in the side wall 62 of the foot support and into respective openings 87 in the hinged cam member 66. These fasteners provide a rigid means of stabilizing the cam member in the space between the foot support and the fixed support plate 44.

Thus, the foot support 14 and the cam member 66 are able to rotate relative to the lower leg support 22 about the axis 42 through the ankle joint.

FIGS. 1 and 2 illustrate one embodiment of the cam member 66 in which the angled cam surfaces 68 and 70 each extend at an angle with respect to a horizontal axis through the shoulder 58 on the rigid support plate 44. Each cam member provides an indexing means located near each angled cam surface indicating the degree measurement the surface is angled.

In the embodiment of FIG. 1 and FIGS. 4 through 7, the cam member 66 is illustrated with cam surfaces 68 and 70 each extending at an acute angle relative to the horizontal axis through the shoulder 58. The apex of each acute angle is on a vertical axis 88 extending through the ankle axis of rotation 42. As the front portion of the cam member rotates upwardly toward the shoulder, the cam surface 68 at the anterior of the cam member rotates into contact with the shoulder, which acts as a rigid stop to limit further angular rotation of the cam member and the foot support relative to the lower leg support. This angular motion is in dorsiflexion as indicated by the angle D in FIG. 1 which represents the limited motion of the orthosis about the ankle joint as limited by the cam surface 68. Similarly, as a posterior portion of a cam member rotates upwardly toward the shoulder the cam surface 70 rotates into contact with the shoulder, which acts as a rigid stop to limit further rotation of the cam member and the foot support in plantar flexion. This angular motion is indicated by the angle P in FIG. 1 and illustrates the limited range of motion controlled by the angle of the cam surface 70 of the cam member 66.

FIGS. 8 through 17 illustrate various forms of a set of cam members that are interchangeable in the recessed space 64 and the inside face 62 of the foot support for controlling varying degrees of motion in plantar and dorsiflexion for the ankle-foot orthosis.

Figure 8:
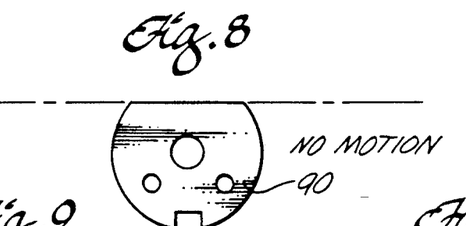
FIGS. 8 through 17 comprise elevation views illustrating various combinations of anterior and posterior cam surfaces for use in selectively adjusting varying degrees of motion about an axis through the ankle joint.

FIG. 8 illustrates a cam 90 that can be used on lateral and medial sides of the orthosis for immobilizing the foot support relative to the leg support to thereby produce no angular motion about the axis through the ankle joint.

Figure 9:
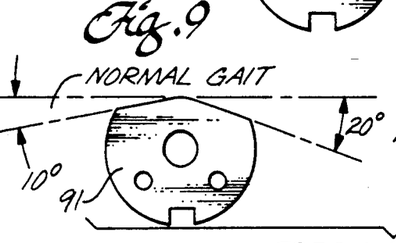

FIG. 9 illustrates a cam 91 that can be used to set a normal gait in dorsiflexion and plantar flexion. In this embodiment motion is limited to 20° in plantar flexion and 10° in dorsiflexion.

Figure 10:
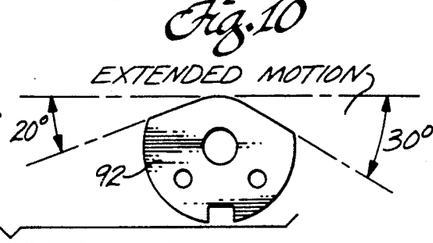

FIG. 10 illustrates a cam 92 that can be used for extended ranges of motion in plantar flexion and dorsiflexion. In this embodiment, motion is limited to 30° plantar flexion and 20 dorsiflexion relative to the cam shown in FIG. 9.

Figure 11:
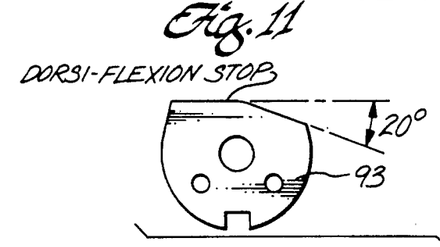

FIG. 11 shows a cam 93 which provides a controlled stop in one direction. In this embodiment the cam produces a stop in dorsiflexion and a limited range of motion of 20° in plantar flexion. Reversing the cam produces a stop in plantar flexion and a limited range of motion of 20° in dorsiflexion.

Figure 12:
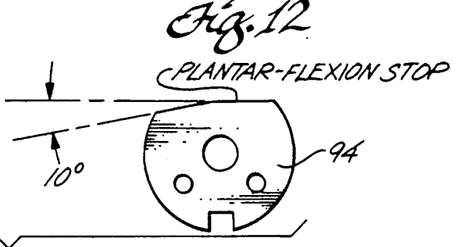

FIG. 12 illustrates a cam 94 having a plantar flexion stop and a limited angular motion in dorsiflexion of 10°. Reversing the cam produces a dorsiflexion stop with a limited range of motion of 10° in plantar flexion.

Figure 13:
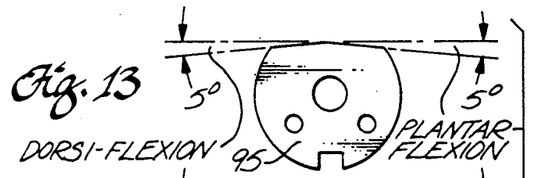

FIGS. 13 through 16 illustrate various embodiments of cam members providing a controlled stop in one direction and varying ranges of motion in the opposite direction. The cam 95 in FIG. 13 shows a 5° controlled stop in dorsiflexion and a 5° range of motion in plantar flexion.

Figure 14:
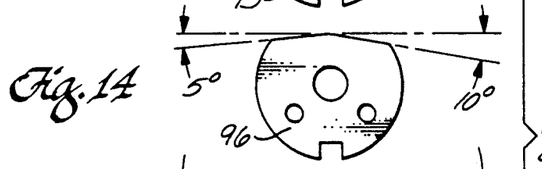

The cam 96 in FIG. 14 provides dual controlled stops in dorsiflexion and plantar flexion in plantar flexion.

Figures 15, 16:
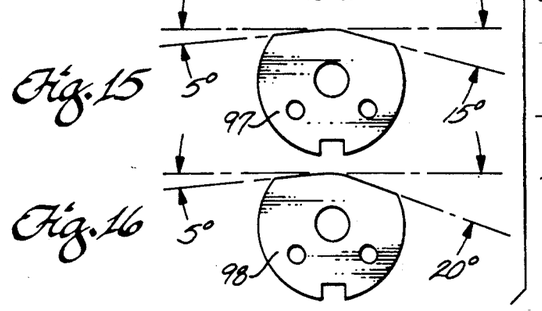

The cam 97 shown in FIG. 15 provides the same controlled stop in dorsiflexion with a further increase to 15° of rotation in plantar flexion.

The cam 98 in FIG. 16 is used to extend the range of motion to 20° for plantar flexion while maintaining the same 5° controlled stop in dorsiflexion.

Other examples are possible. Increases in range of motion, for example, can be achieved by grinding a cam as desired by the orthotist.

Figure 17:
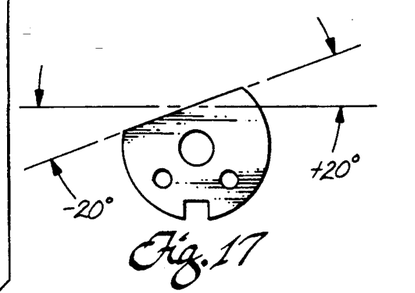

FIG. 17 shows a cam 99 with a (+) and (−) capability. This cam provides flexibility when needs arise to lessen the angular motion control, such as when the patient changes shoes with a different heel height. The addition of 20° above 0° (+) allows the orthotist to alter (increase) the angular stop of the tibia in relation to the foot by grinding off the (+) surface to meet the increase in lift desired.

Thus, the invention enables the orthotist to fabricate a custom made articulating ankle-foot orthosis in a one-step vacuum-forming process. By selection of the proper pair of cams, the orthosis can be altered with varying degrees of motion in plantar and dorsiflexion. Each pair of cams can be color matched and the shoulder of the uprights can be contoured to give good cosmesis with a snug fit.

What is claimed is:

1. A controlled motion orthosis assembly for use in an orthosis for supporting motion about a single axis of rotation through a bodily joint between first and second bodily members on opposite sides of the joint, in which the orthosis includes a first support for attachment to the first bodily member and a second support for attachment to the second bodily member, the controlled motion orthosis assembly comprising:

an elongated rigid support plate for extending continuously from the first support, across the joint axis of rotation, and to the second support;

means for rigidly affixing a first portion of the support plate to the first support on one side of the axis of rotation;

the rigid support plate having an elongated outwardly projecting shoulder for forming a stop facing toward the second support and providing a hard stop in both angular directions of rotation about said single axis of rotation;

a rigid cam positioned to overlap the axis of rotation and adapted for fastening to the second support and for positioning adjacent the rigid support plate and the shoulder thereon;

means pivotally securing the cam and the second support to the support plate so the second support and the cam rotate in unison, relative to the support plate and the first support, about said single axis of rotation;

the shoulder of the support plate facing toward the cam and extending anteriorly and posteriorly relative to the single axis of rotation through the pivot means;

the cam having first and second cam surfaces on opposite sides of the single pivot axis confronting the shoulder on the support plate so that rotation of the second support in one direction about the axis causes the first cam surface to rotate through a first angle and into contact with the shoulder to act as a rigid stop to limit rotation of the second support about said axis to a specific first angle, and so that rotation of the second support in an opposite direction about the axis causes the second cam surface to rotate through a second angle and into contact with the shoulder to act as a rigid stop to limit rotation of the second support about said axis to a specific second angle, thereby controlling swing angles in both anterior and posterior range of motion;

the cam being releasable from attachment to the support plate and the second support so that the cam can be replaced with another cam having first and second cam surfaces at one or more different angles to limit the relative rotation to different first or second angles.

2. Apparatus according to claim 1 including means for rigidly securing the cam to the second support.

3. A controlled motion ankle-foot orthosis for supporting motion about a single axis through the ankle joint, comprising:

a leg support for releasable attachment to the lower leg above the ankle joint;

a foot support for releasable attachment to the foot;

an elongated rigid support plate extending continuously from the leg support, across the ankle joint, and to the foot support;

means for rigidly affixing a first portion of the rigid support plate to the leg support above the axis of rotation through the ankle joint;

the rigid support plate having an outwardly projecting shoulder facing toward the foot support for forming a hard stop in both angular directions of rotation about said single axis of rotation;

a rigid cam positioned for overlapping the ankle joint and removably positioned adjacent the rigid support plate and the foot support, the cam being rigidly fastened to the foot support and for positioning of the cam adjacent the shoulder on the rigid support plate;

means pivotally securing the cam and its attached foot support to the rigid support plate so that foot support and the cam rotate in unison, relative to the support plate and leg support, about said single axis of rotation through the pivot means substantially aligned with the axis of rotation of the ankle joint;

the shoulder of the support plate facing toward the cam and extending anteriorly and posteriorly relative to the axis of rotation through the pivot means;

the cam having anterior and posterior cam surfaces on opposite sides of the single pivot axis of rotation and confronting the shoulder on the rigid support plate so that rotation of the foot support in one direction about the axis of rotation causes the anterior cam surface to rotate into contact with the shoulder anterior of said axis to act as a rigid stop to limit rotation in dorsiflexion to a controlled angle, and so that rotation of the foot support in an opposite direction about the axis of rotation causes the posterior cam surface to rotate into contact with the shoulder posterior of said axis to act as rigid stop to limit angular rotation in plantar flexion to a controlled angle;

the cam being releasable from its attachment to the rigid support plate and its attachment to the foot support so the cam can be replaced with another cam for selectively adjusting either or both angles of rotation in dorsiflexion and plantar flexion.

4. Apparatus according to claim 3 including a plurality of cams each individually adapted for mounting in a position relative to the stop to provide controlled angular motion in dorsiflexion only, in plantar flexion only and in both dorsiflexion and plantar flexion.

5. Apparatus according to claim 4 including multiple cams each for controlling a unique combination of angular motion in both dorsiflexion and plantar flexion in which the different cams are color coded.

6. Apparatus according to claim 3 including means for rigidly securing the cam to the foot support.

7. A controlled motion orthosis assembly for controlling angular motion between first and second orthotic support members adapted for attachment to bodily members on opposite sides of a bodily joint, comprising:

an elongated rigid support adapted to extend from the first orthotic support member across a single axis of rotation of the bodily joint and to the second orthotic support member;

fastening means on the support plate for rigidly securing the support plate to the first orthotic support member spaced from the single axis of rotation through the bodily joint;

an elongated shoulder projecting from a face of the support plate for extending anteriorly of and posteriorly of the bodily joint, the shoulder providing a rigid stop in both angular directions of rotation about said single axis of rotation;

a set of individual cam members each adapted for selective positioning between the support plate and the second orthotic support member, each cam member having means for releasably but rigidly securing the cam member to the second orthotic support member, the cam member being adapted for releasably but rigidly securing the cam member to the second orthotic support member, the cam member being adapted for positioning adjacent the rigid support plate and the shoulder thereon; and means pivotally securing the cam member and the second orthotic support member to the support plate so the cam member and the attached second orthotic support member rotate in unison relative to the first orthotic support member about said single axis of rotation;

the cam members having separate combinations of anterior and posterior can surfaces extending anteriorly and posteriorly of the single joint axis of rotation and adapted for positioning adjacent the shoulder of the support plate so that rotation of the cam member in a first direction about the joint axis causes the first cam surface to engage or rotate into engagement with the first shoulder to act as a rigid stop to limit the angle of rotation in a first direction, and so that rotation of the cam member in a second direction about the joint single axis of rotation causes the second cam member to engage or rotate into engagement with the shoulder to act as a rigid stop to limit the angle of rotation in a second direction, the set of cam members providing different combinations of anterior and posterior cam surfaces so that each individual cam member can be releasably fastened to the second orthotic support member and engaged with the support plate to control a unique combination of rotation about the axis in the first and second directions.

8. The assembly according to claim 7 including fastening means for rigidly securing the cam member to the second orthotic support member spaced from the joint axis of rotation.

9. The assembly according to claim 7 in which different cam members are color coded to identify their respective cam surface combinations.

10. The assembly according to claim 7 including indexing means adjacent the anterior and posterior cam surfaces on each cam member to identify the angle through which the cam member rotates in the first and second direction.

11. Apparatus according to claim 1 in which the first and second cam surfaces comprise flat peripheral edge surfaces extending at an angle to each other and adapted to rotate into engagement with the shoulder on the support plate.

12. Apparatus according to claim 3 in which the anterior and posterior cam surfaces comprise flat peripheral edge surfaces of the cam extending at an angle to each other and adapted to rotate into engagement with a flat edge surface of the shoulder on the support plate to provide the hard stops limiting the swing angles in dorsiflexion and plantar flexion.

13. Apparatus according to claim 12 in which the rigid support plate is curved to match the contour of the ankle bone, and the leg and foot supports are thin plastic shells molded to the shape of the patient's lower leg and foot.

14. Apparatus according to claim 7 in which the anterior and posterior cam surfaces comprise flat peripheral edge surfaces of the cam extending at different angles to each other and adapted to rotate into engagement with a flat edge surface of the shoulder on the support plate to provide the hard stops limiting the swing angles in the first and second opposite directions.

15. Apparatus according to claim 14 in which the first and second orthotic support members comprise lower leg and foot supports of an ankle-foot orthosis.

16. Apparatus according to claim 15 in which the lower leg and foot supports comprise plastic shells molded to the shape of the user's lower leg and foot.

17. Apparatus according to claim 16 in which the support plate is curved to match the shape of the user's ankle bone.

* * * * *

UNITED STATES PATENT AND TRADEMARK OFFICE
CERTIFICATE OF CORRECTION

PATENT NO. : 5,044,360
DATED : September 3, 1991
INVENTOR(S) : Wayne R. Janke

It is certified that error appears in the above-identified patent and that said Letters Patent is hereby corrected as shown below:

Abstract, line 13, change "individualy" to
-- individually --.

Column 1, line 63, change "doubleaction" to
-- double-action --.
Column 3, line 38, change "anklefoot" to -- ankle-foot --.

Column 4, line 40, delete "to".

Column 6, line 32, change "20" to -- 20° --.

In the Claims

Column 8, line 40, after "as" insert -- a --.

UNITED STATES PATENT AND TRADEMARK OFFICE
CERTIFICATE OF CORRECTION

PATENT NO. : 5,044,360

DATED : September 3, 1991

INVENTOR(S) : Wayne R. Janke

It is certified that error appears in the above-identified patent and that said Letters Patent is hereby corrected as shown below:

Column 9, lines 14-16, after "being" delete "adapted for releasably but rigidly securing the cam member to the second orthotic support member, the cam member being"

Signed and Sealed this

Ninth Day of March, 1993

Attest:

STEPHEN G. KUNIN

Attesting Officer

Acting Commissioner of Patents and Trademarks